United States Patent
Ling et al.

(10) Patent No.: US 9,770,533 B2
(45) Date of Patent: Sep. 26, 2017

(54) FABRICATION OF BONE REGENERATION SCAFFOLDS AND BONE FILLER MATERIAL USING A PERFUSION FLOW SYSTEM

(71) Applicant: Southwest Research Institute, San Antonio, TX (US)

(72) Inventors: Jian Ling, Spring Branch, TX (US); Ben Antebi, Helotes, TX (US); Xingguo Cheng, San Antonio, TX (US); Jeffrey N. Harris, San Antonio, TX (US); Xiao-Dong Chen, San Antonio, TX (US)

(73) Assignee: SOUTHWEST RESEARCH INSTITUTE, San Antonio, TX (US)

(*) Notice: Subject to any disclaimer, the term of this patent is extended or adjusted under 35 U.S.C. 154(b) by 0 days.

(21) Appl. No.: 14/728,336

(22) Filed: Jun. 2, 2015

(65) Prior Publication Data
US 2015/0343117 A1    Dec. 3, 2015

Related U.S. Application Data

(63) Continuation of application No. 13/720,543, filed on Dec. 19, 2012, now Pat. No. 9,044,530.

(51) Int. Cl.
*A61L 27/24* (2006.01)
*A61L 27/46* (2006.01)
(Continued)

(52) U.S. Cl.
CPC ........... *A61L 27/46* (2013.01); *A61L 27/3821* (2013.01); *A61L 27/54* (2013.01); *A61L 27/56* (2013.01);
(Continued)

(58) Field of Classification Search
CPC ........... C12N 2533/18; C12N 2521/00; A61L 27/46; A61L 27/3821; A61L 27/54; A61L 27/56; A61L 2430/02
See application file for complete search history.

(56) References Cited

U.S. PATENT DOCUMENTS 8,815,594 B2    8/2014    Harris et al.
9,044,530 B2    6/2015    Ling et al.
(Continued)

OTHER PUBLICATIONS

Antebi, et al "Biomimetic Collagen-Hydroxyapatite Composite Fabricated Via a Novel Perfusion-Flow Mineralization Technique"; Tissue engineering Part C, vol. 19, No. 7 (online ahead of editing Nov. 16, 2012) pp. 487-496.
(Continued)

*Primary Examiner* — Kara Johnson
(74) *Attorney, Agent, or Firm* — Grossman, Tucker et al

(57) ABSTRACT

The present disclosure is directed at a process to form bone grafting material. One may provide a porous collagen scaffold and insert the scaffold into a perfusion chamber of a perfusion flow system. This may then be followed by continuously providing a mineralization perfusion fluid flow through the scaffold at a flow rate to provide dynamic intrafibrillar mineralization of the scaffold and form a collagen/hydroxyapatite composite scaffold. One may optionally provide the scaffold with bone tissue forming cells and then deliver a perfusion fluid including oxygen and one or more nutrients through the collagen/hydroxyapatite composite scaffold and to the bone tissue forming cells at a flow rate such that the bone tissue forming cells remodel the collagen/hydroxyapatite composite scaffold and form a bone tissue extracellular matrix. The bone tissue extracellular matrix may then be decellularized to form an acellular bone repair scaffold.

15 Claims, 14 Drawing Sheets
(5 of 14 Drawing Sheet(s) Filed in Color)

(51) Int. Cl.
A61L 27/54 (2006.01)
A61L 27/38 (2006.01)
A61L 27/56 (2006.01)
(52) U.S. Cl.
CPC ..... A61L 2300/412 (2013.01); A61L 2430/02 (2013.01)

(56) References Cited

U.S. PATENT DOCUMENTS

| | | |
|---|---|---|
| 9,456,893 B2 | 10/2016 | Ling |
| 2008/0025956 A1 | 1/2008 | Yoder et al. |
| 2010/0168872 A1 | 7/2010 | Brown et al. |
| 2010/0279268 A1 | 11/2010 | Neumann et al. |
| 2011/0014597 A1 | 1/2011 | Frerich |
| 2011/0033927 A1 | 2/2011 | Rolle et al. |
| 2013/0030548 A1 | 1/2013 | Ling |
| 2014/0161841 A1 | 6/2014 | Harris et al. |
| 2014/0170117 A1 | 6/2014 | Ling |
| 2015/0050736 A1 | 2/2015 | Harris et al. |

OTHER PUBLICATIONS

Auger, et al., "Tissue-engineered skin substitutes: from in vitro constructs to in vivo applications," Biotechnol. Appl. Biochem., 39. (2004) pp. 263-275.
Badylak, et al, "Extracellular Matrix as a Biological Scaffold Material: Structure and Function"; ScienceDirect, Acta Biomaterialia, vol. 5, 2009, pp. 1-13.
Baht et al., "Bone Sialoprotein-collagen Interaction Promotes Hydroxyapaptite Nucleation", Matrix Biology, vol. 27 (2008) pp. 600-608.
Cartmell, et al; "Effects of Medium Perfusion Rate on Cell-Seeded Three-Dimensional Bone Constructs In Vitro"; Tissue Engineering, vol. 9, No. 6 (2003), pp. 1197-1203.
Cannillo, et al, "Fabrication of 45S5 Bioactive Glass-Polycaprolactone Composite Scaffolds"; 17th International Conference on Composite Materials (ICCM-17), Edinburgh (UK), Jul. 27-31, 2009 (downloaded Jul. 19, 2012 http://www.iccm-central. org/Proceedings/ICCM17proceedings/Themes/Applications/BIOMEDICAL%20APPLICATIONS/B1.5A%20Cannillo.pdf).
Chen, et al; "Extracellular Matrix Made by Bone Marrow Cells Facilitates Expansion of Marrow-Derived Mesenchymal Progenitor Cells and Prevents Their Differentiation Into Osteoblasts"; Journal of Bone and Mineral research, vol. 22, No. 12, 2007 pp. 1943-1956.
Chen, et al "Tissue Engineering of Cartilage Using a Hybrid Scaffold of Synthetic Polymer and Collagen." Tissue Engineering, vol. 10, No. 314 (2004) pp. 323-330.
Clarke, Bart , "Normal Bone Anatomy and Physiology", Clinical Journal of the American Society of Nephrology, vol. 3, 2008, S131-S139.
Colfen, Helmut , "A Crystal-Clear View", Nature Materials, News & Views; vol. 9, , Dec. 2010, 2010, 960-961.
Colton, "Implantable biohybrid artificial organs," Cell Transplant, vol. 4, No. 4. (1995) pp. 415-436.
Du, C. et al., "Formation of Calcium Phosphate/Collagen Composites Through Mineralization of Collagen Matrix", John Wiley & Sons, Inc.,, 2000, 518-527.
Fizgerald, "Collagen in wound healing: are we onto something new or just repeating the past?" The Foot and Ankle Online Journal, 2(9):3 (2009).
Gower, Laurie B. , "Biomimetic Model Systems for Investigating the Amorphous Precursor Pathway and Its Role in Biomerization", 2008 American Chemical Society, Chem, Rev 2008, 108, 2008, 4551-4627.
Hirschi, et al., "PDGF, TGF-beta, and heterotypic cell-cell interactions mediate endothelial cell-induced recruitment of 10T1/2 cells and their differentiation to a smooth muscle fate," J Cell Biol, 141(3), (1998) pp. 805-814.

Hokugo, et al "Preparation of Hybrid Scaffold From Fibrin and Biodegradable Polymer Fiber", Biomaterials, vol. 27 (2006), pp. 61-67.
Huang, Zhi et al., "A Bone-like Nano-hydroxyapatite/collagen Loaded Injectable Scaffold", IOP Publishing, Biomedical materials, Biomed Mater, 4, 2009, 1-7.
Jiao, et al: "Fabrication and Characterization of PLLA-chitosan Hybrid Scaffolds With Improved Cell Compatibility"; InterScience, Journal of Biomedical Materials Research Part A, vol. 80A, No. 4 (online Oct. 20, 2006) pp. 820-825.
Karperien, et al; "Morphogenesis, Generation of Tissue in the Embryo"; Elsevier/Academic Press, Tissue Engineering, Senior Editor C.vanBlitterswijk; 2008 San Diego, CA, Book Publication Info and pp. 58-62.
Kashfi, et al, "A Review of Various Techniques of Orthotopic Liver Transplantation in the Rat"; Transplantation Proceedings, vol. 37, 2005, pp. 185-188.
Kikuchi, Masanori et al., "Self-organization Mechanism in a Bone-like Hydroxyapatite/collagen Nanocomposite Synthesized In Vitro and Its Biological Reaction In Vivo", Elsevier, Biomaterials 22 (2001), 2001, 1705-1711.
Koch, et al, "Fibrin-polylactide-based Tissue-engineered Vascular Graft in the Arterial Circulation", Biomaterials, vol. 31, pp. 4731-4739 (2010).
Kumar, et al., "Plastic surgery challenges in war wound," Advanced in Wound Care, 1, (2010) pp. 65-70.
Lai, et al; "Reconstitution of Marrow-Derived Extracellular Matrix Ex Vivo: A Robust Culture system for Expanding Large-Scale Highly Functional Human Mesenchymal Stem Cells"; Stem Cells and Development, vol. 19, No. 7, 2010, pp. 1095-1108.
Lange, et al, "Liver-Specific Gene Expression in Mesenchymal Stem Cells is Induced by Liver Cells"; World Journal of Gastroenterology, 2005, vol. 11, No. 29; pp. 4497-4504.
Lantz, et al., "Small intestinal submucosa as a vascular graft: a review," J. Invest. Surg., 6(3), (1993) pp. 297-310.
Lee et al, "Designed Hybrid Scaffolds Consisting of Polycaprolactone Microstrands and Electrospun Collagen-Nanofibers for Bone Tissue Regeneration"; Journal of Biomedical Materials Research, Applied Biomaterials/ vol. 97B, Issue 2, (online Mar. 7, 2011—pp. 263-270).
Lees, Sidney et al., "A Study of Some Properties of Mineralized Turkey Leg Tendon", 1992 Gordon and Breach Science Publishers S.A.; Connective Tissue Research 1992, vol. 28, 1992, 263-287.
Liao et al, "Fabricaiton of Porous Biodegradable Polymer Scaffolds Using a Solvent Merging/Particulate Leaching Method.", Journal of Biomedical Materials Research, vol. 59, No. 4 (2001), pp. 676-681.
Lickorish, David , "Collagen-hydroxyapatite Composite Prepared by Biomimetic Process", Wiley Periodicals, Inc., J. Biomed Mater Res, 2003, 19-27.
Linke, et al, "Engineered Liver-Like Tissue on a Capillarized Matrix for Applied Research"; Tissue Engineering, vol. 13, No. 11, 2007, pp. 2699-2707.
Lockmic, et al., "An arteriovenous loop in a protected space generates a permanent, tightly vascular, tissue-engieered construct," FASEB, 21(2). (2007) pp. 511-522.
Luo, et al., "A multi-step method for preparation of porcine small intestinal submucosa (SIS)," Biomaterials, 32, (2011) pp. 706-713.
Markowicz, et al., "Enhancing the vascularization of three-dimensional scaffolds: new strategies in tissue regeneration and tissue engineering," Topics in Tissue Engineering, vol. 2, Chapter 6, \Eds. Ashammakhi N Reis RL.—2005 (15 pages).
Mikos, et al, "Preparation and Characterization of Poly(L-lactic acid)foams". Polymer, vol. 35, No. 5 (1994) pp. 1068-1077.
Moon, et al., "Vascularization of engineered tissues: approaches to promote angiogenesis in biomaterials," Current Topics in Medicinal Chemistry, 8(4), (2008) pp. 300-310.
Nillesen, et al., "Increased angiogenesis and blood vessel maturation in acellular collagne-heparin scaffolds containing both FGF2 and VEGF," Biomaterials, 28, (2007) pp. 1123-1131.
Olszta, Matthew J. et al., "Bone Structure and Formation: A New Perspective", Elsevier, Science Direct; Reports: A Review Journal, Materials Science and Engineering, R 58, 2007, 77-116.

(56) References Cited

OTHER PUBLICATIONS

Ozawa, Hidehiro et al., "Current Concepts of Bone Biomineralization", J. Oral Bioscience, 50(1), 2008, 1-14.
Paige, et al., "Engineering new tissue: formation of neocartilage," Tissue Eng., 1, (1995) pp. 97-106.
Park, et al., "Tissue engineering of urinary organ," Yonsei Med. J., 41, (2000) pp. 780-788.
Pek, Y.S. et al., "Porous Collagen-apatite Nanocomposite Foams as Bone Regeneration Scaffolds", Elsevier Biomaterials 29, 2008, 4300-4305.
Praetorius, et al; "Bending the MDCK Cell Primary Cilium Increases Intracellular Calcium"; Journal of Membrane Biology, vol. 184, 2001, pp. 71-79.
Prosecka, E. et al., "Optimized Conditions for Mesenchymal Stem Cells to Differentiate Into Osteoblasts on a Collagen/hydroxyapatite Matrix", Wiley Periodicals, Inc., Society for Biomaterials, J. Biomed Mater Res Part A 2011:99A, 2011, 307-315.
Raghavan, et al., "Physical characteristics of small intestinal submucosa scaffolds are location dependent," J. Biomed. Mater. Rec. A, 73, (2005) p. 90-96.
Ratcliffe, "A Tissue engineering of vascular grafts," Matrix Biol., 19, (2000) pp. 353-357.
Rodrigues, et al, "Characterization of a Bovine Collagen-Hydroxyapatite Composite Scaffold for Bone Tissue Engineering", Biomaterials, vol. 24, pp. 4987-4997 (2003).
Roeder, et al., "Compliance, elastic modulus, and burst pressure of small-intesine submucosa (SIS), small-diameter vascular grafts," J. Biomed Mater Res, 45.—(1999) p. 65-70.
Sakiyama-Elbert, et al., "Development of fibrin derivatives for controlled release of heparin-binding growth factors," J. Control. Release, 65, (2000) pp. 389-402.
Sikavitsas, et al "Mineralized Matrix Deposition by Marrow Stromal Osteoblasts in 3D Perfusion Culture Increases With Increasing Fluid Shear Forces."; Proceedings of the National Academy of Sciences, vol. 100, No. 25 (Dec. 9, 2003) pp. 14683-14688.
Slaughter, et al, "Hydrogels in Regenerative Medicine"; Advanced Materials 2009, vol. 21, pp. 3307-3329.
Thula, Taili T. et al., "In Vitro Mineralization of Dense Collagen Substrates: A Biomimetic Approach Toward the Development of Bone-graft Materials", Elsevier, Science Direct; Acta Biomaterialia, Inc. 7, 2011, 3158-3169.
Thula, T., et al, "Mimicking the Nanostructure of Bone: Comparison of Polymeric Process-Directing Agents", Polymers, vol. 3, pp. 10-35 (2011).
Tsigkou, et al., "Engineered vascularized bone grafts," PNAS, 107(8), (2010) pp. 3311-3316.
Viguet-Carrin, S. et al., "The Role of Collagen in Bone Strength", Osteoporos International (2006) 17, Dec. 9, 2005, 319-336.
Wang, et al; "A Hybrid Scaffold of Poly(Lactide-CO-Glycolide) Sponge Filled With Fibrin Gel for Cartilage Tissue Engineering"; Chinese Journal of Polymer Science, vol. 29, No. 2, 2011, pp. 233-240.
Wang, et al., "Osteogenesis and angiogenesis of tissue engineered bone construct by prevascularized β-tricalcium phosphate scaffold and mensenchymal stem cells," Biomaterials, 31, (2010) pp. 9452-9461.
Yamauchi, Kiyoshi et al., "Preparation of Collagen/Calcium Phosphate Multilayer Sheet Using Enzymatic Mineralization", Elsevier Ltd., Biomaterials, 2004, 5481-5489.
Yu, D, et al, "Bladder Wall Grafting in Rats Using Salt-modified and Collagen-coated Polycaprolactone Scaffolds Preliminary Report", International Journal of Urology (2007), vol. 14, pp. 939-944.
US Office Action issued in U.S. Appl. No. 13/720,543, mail date Aug. 13, 2013 (14 pgs).
US Office Action issued in U.S. Appl. No. 13/712,583, mail date Oct. 23, 2013 (12 pgs).
US Office Action issued in U.S. Appl. No. 13/720,543, mail date Apr. 8, 2014 (12 pgs).
US Office Action issued in U.S. Appl. No. 13/194,348, mail date Jul. 24, 2014 (13 pgs).
US Office Action issued in U.S. Appl. No. 13/720,543, mail date Sep. 23, 2014 (11 pgs).
US Office Action issued in U.S. Appl. No. 13/194,348, mail date Oct. 28, 2014 (15 pgs).
US Office Action issued in U.S. Appl. No. 13/194,348, mail date Mar. 31, 2015 (13 pgs).
US Office Action issued in U.S. Appl. No. 14/467,879, mail date Jun. 2, 2015 (13 pgs).
US Office Action issued in U.S. Appl. No. 13/194,348, mail date Oct. 16, 2015 (15 pgs).
US Office Action issued in U.S. Appl. No. 14/467,879, mail date Sep. 26, 2016 (12 pgs).

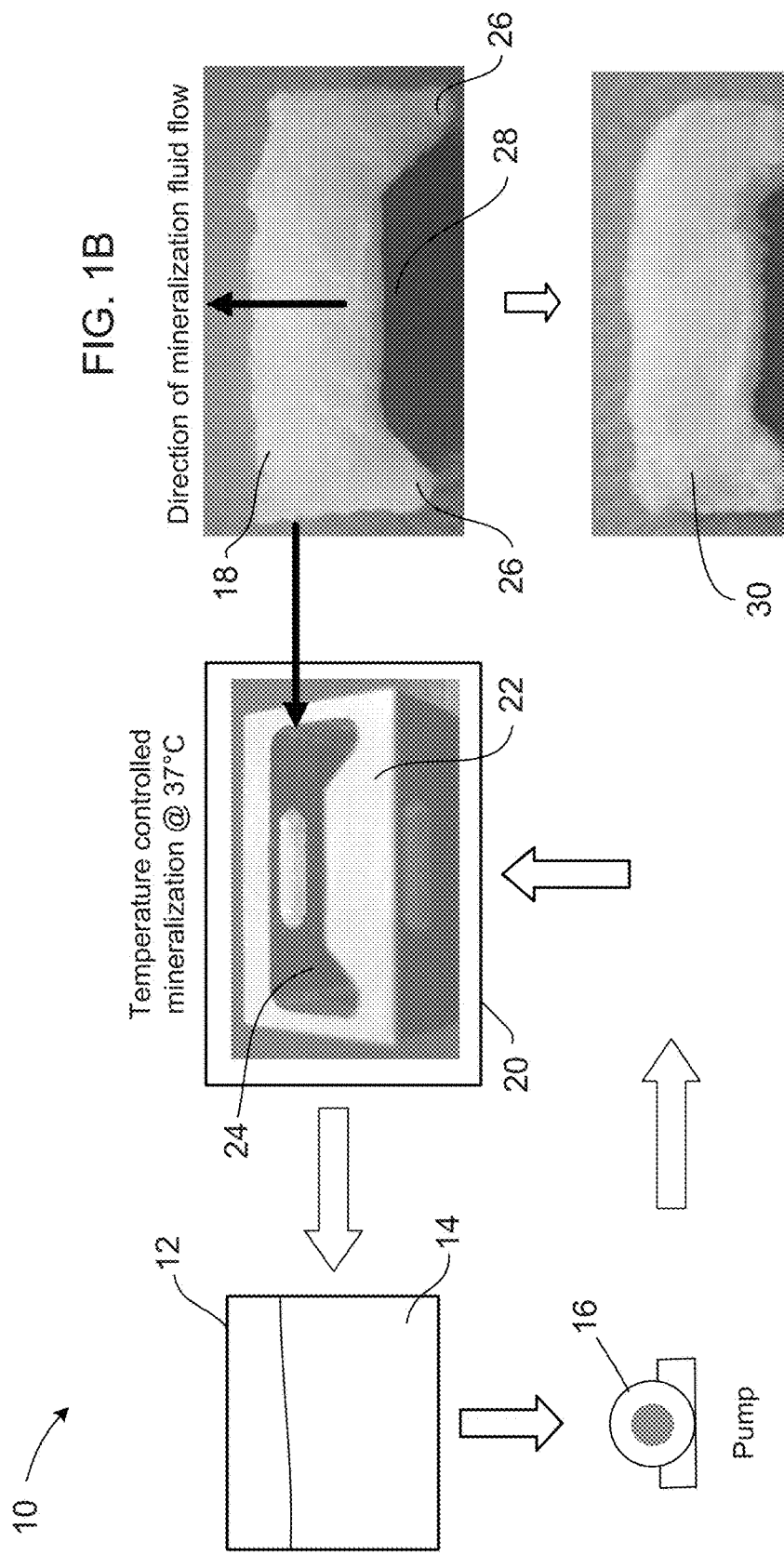

FABRICATION OF BONE REGENERATION SCAFFOLDS AND BONE FILLER MATERIAL USING A PERFUSION FLOW SYSTEM

CROSS REFERENCE TO RELATED APPLICATIONS

This application is a continuation of U.S. application Ser. No. 13/720,543 filed Dec. 19, 2012, now U.S. Pat. No. 9,044,530 B2, the teachings of which are incorporated herein by reference.

STATEMENT OF GOVERNMENT SPONSORSHIP

This invention was made with government support under grant no. 1R21HL102775-01 awarded by the National Institutes of Health. The government has certain rights in the invention.

FIELD OF THE INVENTION

This disclosure relates to fabrication of tissue scaffolds and, more particularly, fabrication of bone regeneration scaffolds and bone filler material.

BACKGROUND

Natural bone composition may be simulated by scaffolds for bone tissue engineering composed of collagen/HA composites. To fabricate a collagen/HA composite, a conventional method may utilize standing mineral solutions that contain supersaturated calcium-phosphate ions to presoak a porous collagen scaffold. However, high calcium-phosphate ion concentrations typically cause the minerals to precipitate out of solution rather than only crystallizing on the collagen scaffold. As a result, the mineral content is deposited on the surface of the collagen fibers rather than within them, which often obstruct the pores of the collagen scaffold.

Another common preparation method premixes collagen and synthetic HA nanoparticles to form collagen-apatite slurry. This mixing technique mechanically blends collagen and HA to form a physical mixture that lacks any chemical bonding. In addition, synthetic HA nanoparticles are often different in crystal size and crystalline phase from the hydroxyapatite found in natural bone. As a result, the collagen/HA composites that are fabricated using this technique are understood to possess poor mechanical properties with diminished osteoconductive and osteoinductive properties.

These conventional in vitro collagen mineralization methods are different from the in vivo bone formation process, and often result in scaffolds that are generally unsuitable for bone tissue engineering.

SUMMARY

The present disclosure is directed at a process to form bone grafting material. One may provide a porous collagen scaffold and insert the scaffold into a perfusion chamber of a perfusion flow system. This may then be followed by continuously providing a mineralization perfusion fluid flow through the scaffold at a flow rate to provide dynamic intrafibrillar mineralization of the scaffold and form a collagen/hydroxyapatite composite scaffold. One may optionally provide the scaffold with bone tissue forming cells and then deliver a perfusion fluid including oxygen and one or more nutrients through the collagen/hydroxyapatite composite scaffold and to the bone tissue forming cells at a flow rate such that the bone tissue forming cells remodel the collagen/hydroxyapatite composite scaffold and form a bone tissue extracellular matrix. The bone tissue extracellular matrix may then be decellularized to form an acellular bone repair scaffold.

The bone grafting materials fabricated herein may be used as an off-the-shelf product for bone repair. When used as bone void fillers, the bone grafting materials containing bone tissue specific extracellular matrix, which may be in acellular form, may accelerate bone healing at a tissue treatment site, particular to accelerate the bone repair/reconstruction/regeneration processes. The bone grafting materials may be made to be substantially similar to a target bone configuration, such as trabecular bone, in composition, porosity level, pore size, and stiffness. The bone grafting materials may also provide properties of stiffness and/or elasticity, particularly to be deformable to a shape of a tissue treatment site of a host and thereafter retain the shape after being deformed thereto. The bone extracellular matrix of the bone grafting materials may promote migration of host cells surrounding the bone grafting material to the bone grafting material for bone regeneration, and promote proliferation of host cells in the bone grafting material. The acellular bone grafting materials may also be seeded with autologous cells of the host before implantation to accelerate bone regeneration, or be implanted directly into a defect without cells.

FIGURES

The patent application file contains at least one drawing executed in color. Copies of this patent application publication with color drawings will be provided by the Office upon request and payment of the necessary fee.

The above-mentioned and other features of this disclosure, and the manner of attaining them, will become more apparent and better understood by reference to the following description of embodiments described herein taken in conjunction with the accompanying drawings, wherein:

FIG. 1A is a schematic representation of a perfusion-flow (i.e., dynamic) system to deliver mineralization solution throughout a porous collagen scaffold;

FIG. 1B is a picture of a collagen scaffold prior to dynamic mineralization;

FIG. 1C is a picture of a collagen scaffold after dynamic mineralization to provide a collagen/HA composite scaffold;

DETAILED DESCRIPTION

Figure 2A:
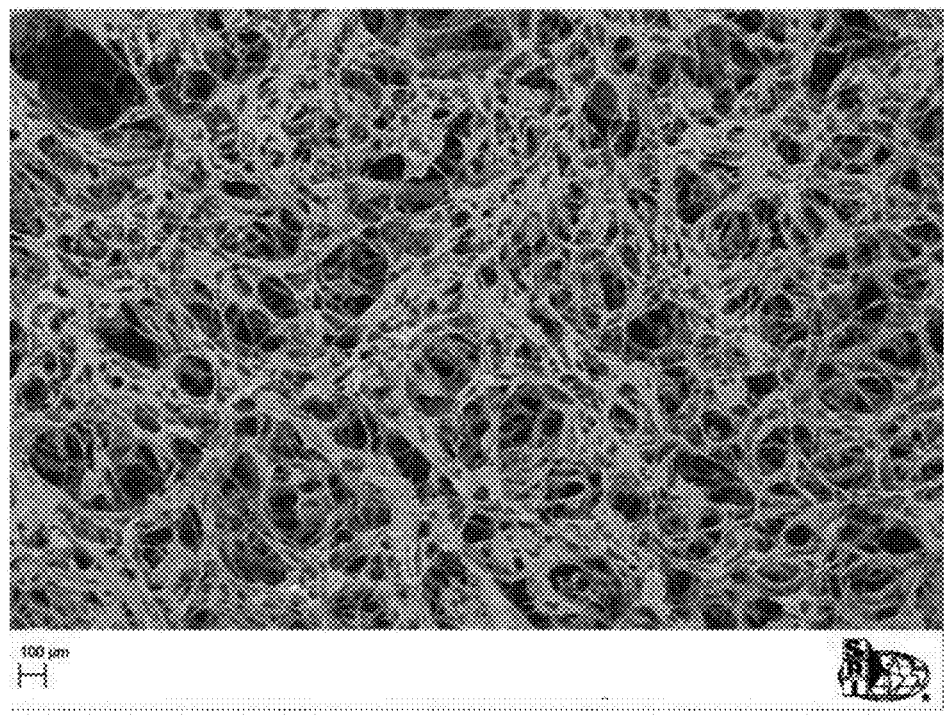
FIG. 2A is an environmental scanning electron microscope (ESEM) image of the non-mineralized collagen scaffold.

It may be appreciated that the present disclosure is not limited in its application to the details of construction and the arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art.

Bone is composed of approximately 70% inorganic mineral, 20% organic matrix, and 10% water. The mineral content of bone is predominantly hydroxyapatite (HA), a naturally occurring mineral form of calcium apatite (phosphate mineral) with the formula $Ca_5(PO_4)_3(OH)$, while the organic matrix is composed mainly of type I collagen (~90%) and small amounts (~10%) of non-collagenous proteins (NCPs). Biomechanically, the inorganic mineral (i.e., HA) endows bone with its rigid structural framework while collagen confers bone with its elastic properties.

The natural bone formation process is comprised of two stages: primary and secondary osteogenesis (or ossification). In primary osteogenesis, bone formation is initiated from preexisting cartilage (i.e., endochondral osteogenesis), in which HA crystals form in an unorganized manner (i.e., woven bone) within proteoglycan matrix and do not form close association with collagen. Therefore, when attempting to mimic the bone formation process using collagen, primary osteogenesis is not discussed. In secondary osteogenesis, the primary woven bone is remodeled into a more organized structure by embedding nanoscopic hydroxyapatite crystals primarily within collagen fibers, a process termed intrafibrillar mineralization.

In bone formation, intrafibrillar mineralization requires NCPs, relatively low concentration of mineral ions, and extracellular fluid (ECF) flow. NCPs, such as osteonectin and osteocalcin, are thought to play a fundamental role in the mineralization process by binding the calcium ions that are present in the ECF, and thereby creating a liquid amorphous calcium phosphate phase, termed polymer-induced liquid-precursor (PILP). Due to the high affinity of the NCPs to collagen and the fluidic character of the PILP, the calcium phosphate precursor can infiltrate into the collagen fibrils. Upon removal of water, the HA crystals, being more thermodynamically stable, crystallize within the collagen fibers.

To emulate the intrafibrillar mineralization process of secondary osteogenesis, a calcium-phosphate solution containing micro-molar amounts of a negatively-charged acidic polypeptide (i.e., polyaspartic acid) may be used. While not being bound to a particular theory, the polyaspartic acid functions as the NCPs in vivo by inhibiting the nucleation of HA crystals within the mineral solution while inducing HA nucleation when attached to the collagen fibers. However, with use of a standing (i.e. non-flowing) mineral solution to emulate the physiological ECF, this static PILP mineralization method is dependent on the penetration depth of the PILP phase, which is limited to a distance of about 100 μm in dense collagen substrates. Thus, the static PILP mineralization method is not suitable for mineralization of collagen scaffolds in sizes that are clinically relevant for tissue engineering applications.

To further improve the intrafibrillar mineralization technique, continuous perfusion flow (referred to as dynamic intrafibrillar mineralization) as disclosed herein may now be used to simulate the flow of the ion-containing ECF that occurs in vivo. The continuous perfusion of the amorphous fluid phase may now replenish the mineral ions to the collagen scaffold, and thereby increases the efficiency of the intrafibrillar mineralization. The perfusion flow also facilitates a relatively uniform mineral deposition throughout the collagen scaffold that results in a relatively homogenous collagen/HA composite. Accordingly, utilizing the perfusion flow method herein, one observes that the difference between the amount of mineral deposition inside the scaffold and the amount of mineral deposition on the outside of the scaffold is relatively lower than what is typically observed utilizing static mineralization techniques.

To demonstrate the benefits of dynamic intrafibrillar mineralization, comparison of efficiency, homogeneity, and mechanical properties of the collagen/HA composites fabricated by static and dynamic intrafibrillar mineralization are compared and provided with this disclosure. Data indicates that the resultant collagen/HA composites prepared by the dynamic intrafibrillar mineralization can now provide a mechanically stable environment that is biocompatible, biodegradable, and suitable for human mesenchymal stem cell (hMSC) growth. It is also now contemplated that collagen/HA composites fabricated via dynamic intrafibrillar mineralization may be configured to resemble, e.g., human trabecular bone both in properties (e.g. stiffness, porosity level, pore size) and composition.

As alluded to above, the present disclosure is directed to the procedure of inserting a collagen scaffold into a perfusion chamber of a closed-loop perfusion flow system and continuously delivering a mineralization perfusion fluid through the collagen scaffold at a flow rate to provide mineralization of the collagen scaffold and forming a collagen/hydroxyapatite composite scaffold. Bone tissue forming cells may be provided on the scaffold. This may then be followed by delivering oxygen and one or more nutrients as components of a remodeling perfusion fluid through the collagen/hydroxyapatite composite scaffold and to the bone tissue forming cells at a flow rate such that the bone tissue forming cells remodel the collagen/hydroxyapatite composite scaffold with a bone tissue extracellular matrix. This may then be followed by terminating delivery of the oxygen and one or more nutrients to the collagen/hydroxyapatite composite scaffold and the bone tissue forming cells and decellurizing (removing cells) and forming the acellular bone repair scaffold.

Referring now to the figures, FIG. 1A shows a schematic representation of an exemplary in vitro closed-loop continuous perfusion-flow (i.e., dynamic) system 10 which comprises a source container 12 of mineralization fluid (liquid solution) 14, which may be circulated by the pump 16 (e.g. peristaltic) at a continuous flow rate to deliver the mineralization fluid 14 to a porous collagen scaffold 18 (see FIG. 1B) contained in a temperature controlled chamber 20, pass the fluid 14 throughout the collagen scaffold 18 and return the fluid 14 to the source container 12. The continuous flow rate may be in the range of 1.0 micrometer/second (1 μm/s) up to 10 mm/s. Reference to such a continuous flow rate herein is reference to the time that is required for the fluid to travel the indicated distance over the indicated time. Particularly advantageous, however, are continuous flow rates of 20 μm/s to 500 μm/s. The temperature-controlled chamber 20 may particularly be maintained at about human body temperature of 37° C. during mineralization, while the rest of the system 10 and mineralization fluid 14 (i.e. the solution outside the chamber 20) may set to ambient temperature (e.g. 20-24° C.) to inhibit crystal growth.

Mineralization may be performed using a tris-based mineralization solution containing 4.2 mM $K_2HPO_4$ (dipotassium phosphate), 9 mM $CaCl_2$ (calcium chloride), and 15 μg/ml of polyaspartic acid. As shown by FIGS. 1A and 1B, within the chamber 20, the collagen scaffold 18, here having a size of 3 mm×3 mm×11 mm, is placed within a mold 22 having a cavity 24 with a geometry corresponding to an outer geometry as the collagen scaffold 18. The side protrusions 26 of the scaffold 18 form a recess 28 in the collagen scaffold 18 to inhibit the solution 14 from flowing around the scaffold 18 rather than through the scaffold 18. As shown in FIG. 1C, the porous collagen scaffold (FIG. 1B) has been mineralized (here for 24 hours) to provide the collagen/HA composite scaffold 30. The mineralization time can be used to regulate the degree of mineralization, and thus the mechanical strength of the composite scaffold 30. Thus, mineralization time may generally be in a range, for example of 12 hours to 7 days, including all values and increments therein. For example, one may continuously flow the mineralization solution for a period of 12 hrs, 24 hrs, 48 hrs, 72 hrs and/or 96 hrs.

Figure 2B:
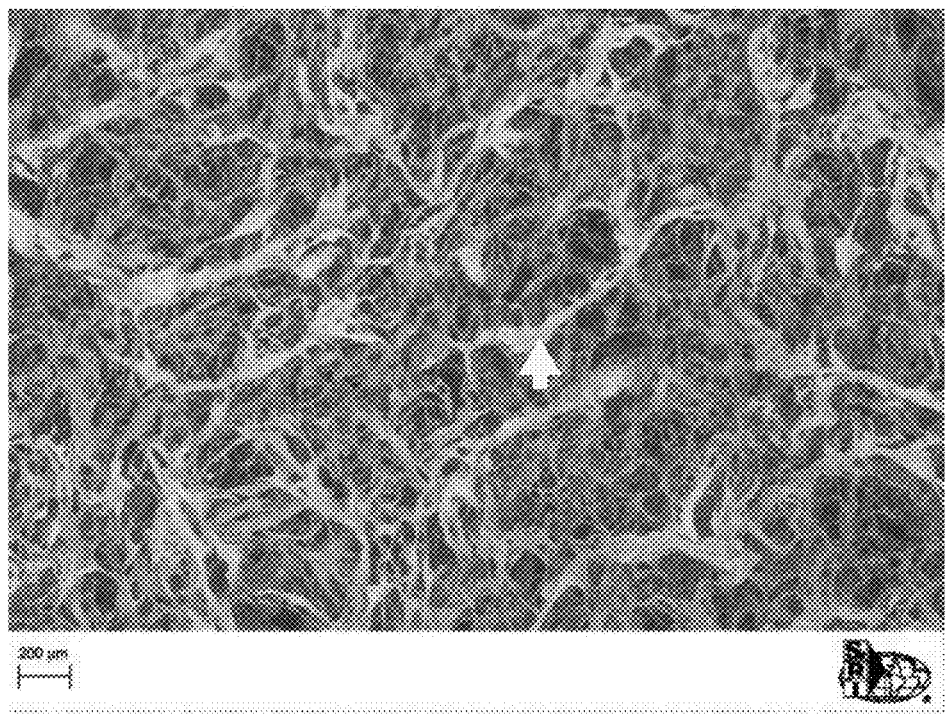
FIG. 2B is an environmental scanning electron microscope (ESEM) image of the collagen scaffold mineralized for 24 hours (dynamic method) to provide the collagen/HA composite scaffold.
Figure 2C:
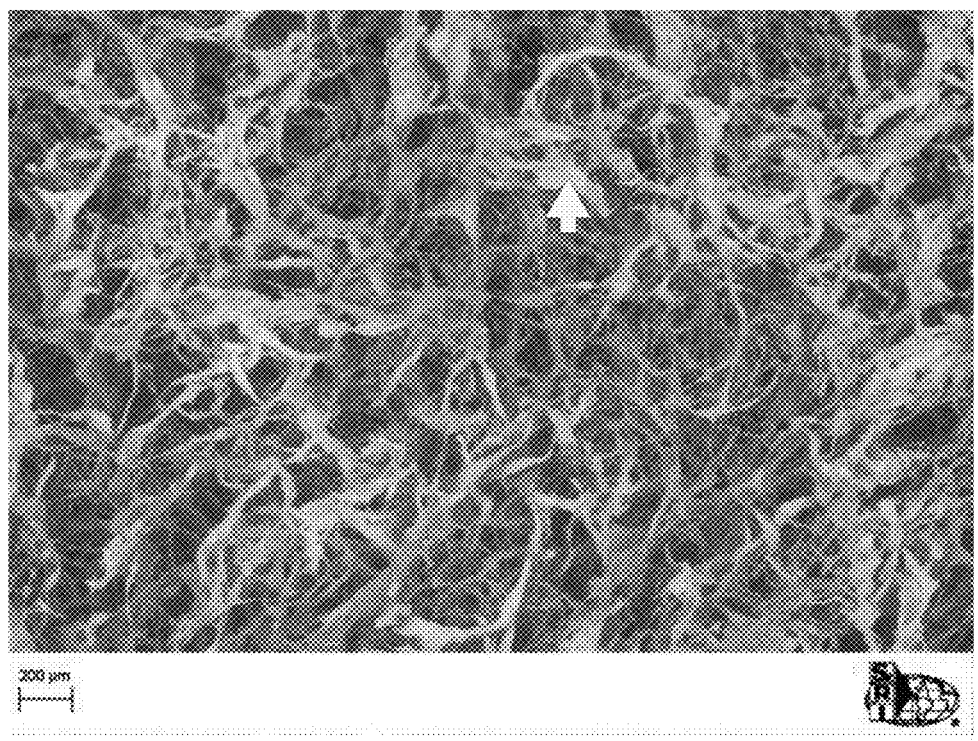
FIG. 2C is an environmental scanning electron microscope (ESEM) image of the collagen scaffold mineralized for 48 hours (dynamic method) to provide the collagen/HA composite scaffold.
Figure 2D:
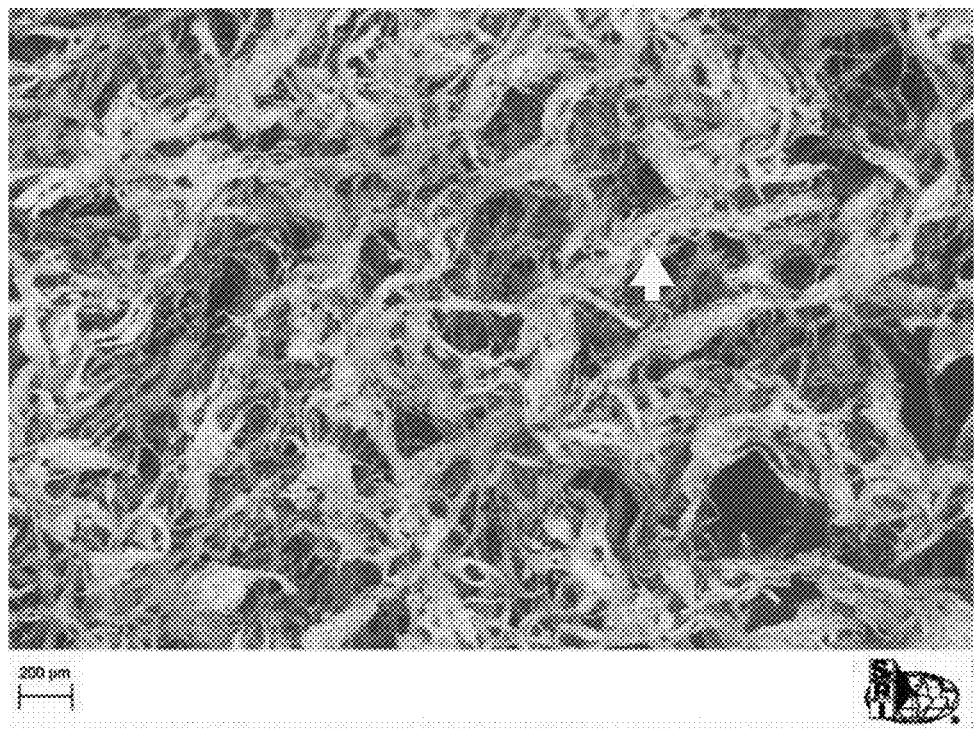
FIG. 2D is an environmental scanning electron microscope (ESEM) image of the collagen scaffold mineralized for 72 hours (dynamic method) to provide the collagen/HA composite scaffold.
Figure 2E:
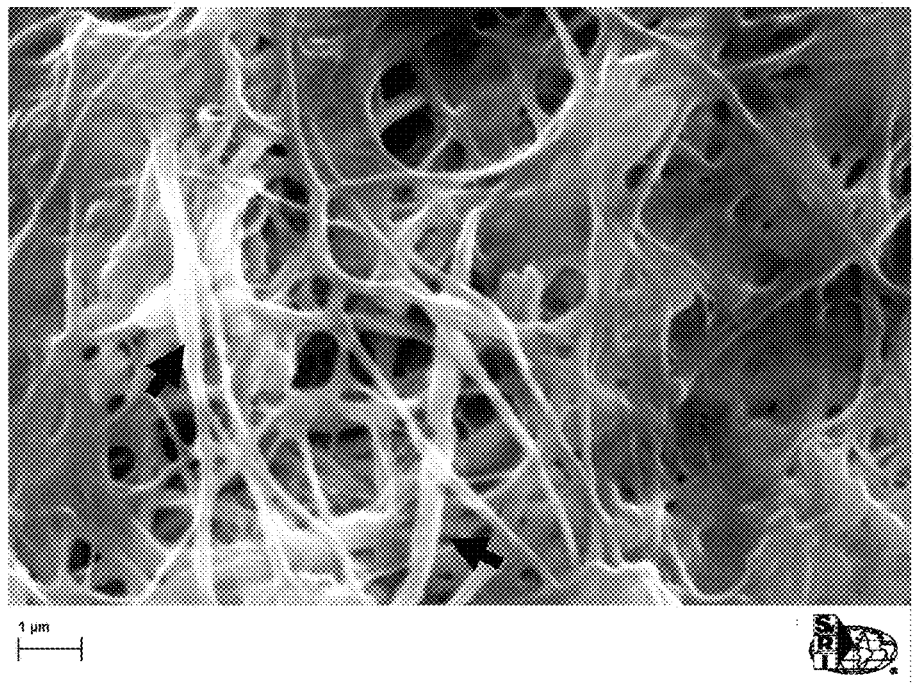
FIG. 2E is an environmental scanning electron microscope (ESEM) image of the collagen scaffold mineralized for 24 hours (static method) to provide the collagen/HA composite scaffold.
Figure 2F:
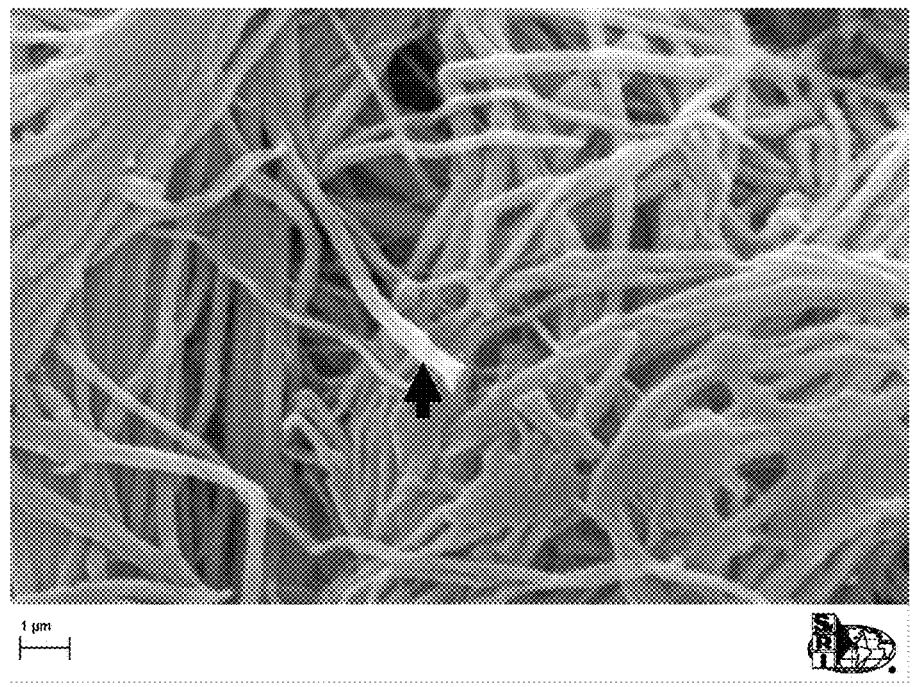
FIG. 2F is an environmental scanning electron microscope (ESEM) image of the collagen scaffold mineralized for 24 hours (dynamic method) to provide the collagen/HA composite scaffold.

FIGS. 2A-2D show Environmental Scanning Electron Microscope (ESEM) images of non-mineralized collagen scaffold 18 (FIG. 2A) and collagen/HA composite scaffold 30 mineralized for 24, 48, and 72 hours, respectively in FIGS. 2B, 2C and 2D. Collagen/HA fiber bundles are indicated by the white arrows in FIGS. 2B to 2D. ESEM images from FIGS. 2B to 2D demonstrate an increasing level of mineralization with the increase in mineralization time. The degree of mineralization is indicated by the thickness of the collagen-hydroxyapatite fibers (i.e., struts). The high magnification ESEM images in FIGS. 2E and 2F compare the mineralization homogeneity of the static (i.e. no perfusion flow) versus dynamic (i.e. with continuous perfusion flow) PILP methods, and indicate a relatively more uniform intrafibrillar mineralization through the dynamic method herein than the static method.

Figures 3A, 3B:
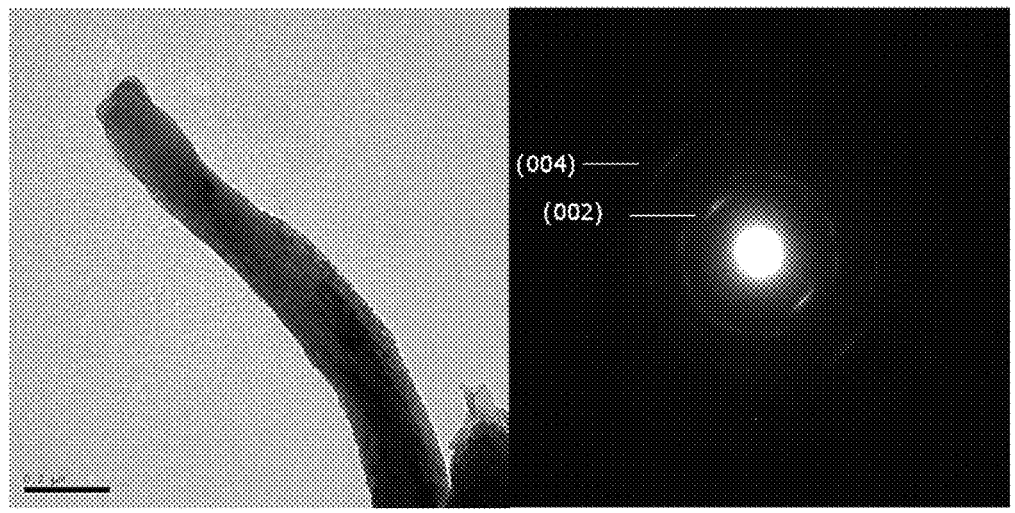
FIG. 3A is a transmission electron micrograph (TEM) using bright field mode of the collagen/HA composite scaffold mineralized for 24 hours via the static mineralization method.
FIG. 3B is a transmission electron micrograph (TEM) using selected area electron defraction (SAED) mode of the collagen/HA composite scaffold mineralized for 24 hours via the static mineralization method.
Figures 3C, 3D:
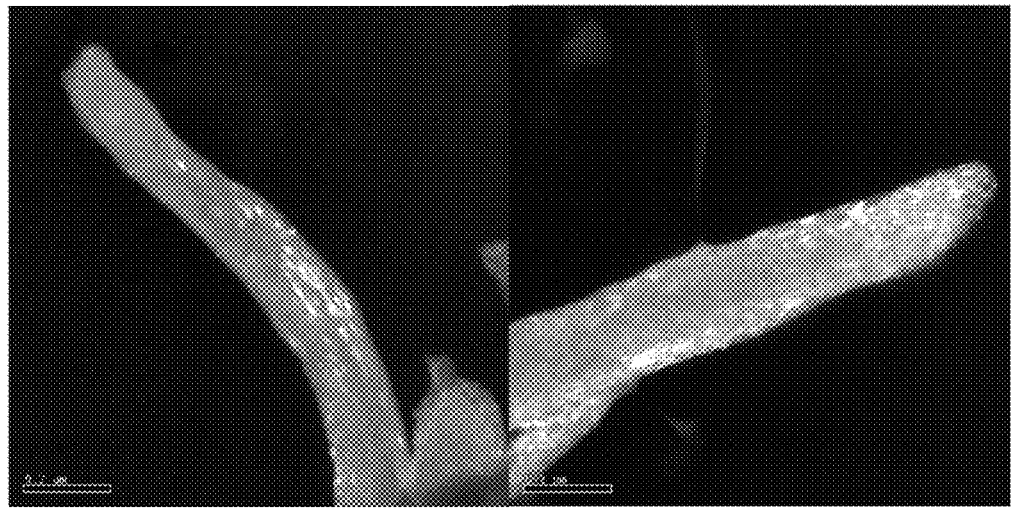
FIG. 3C is a transmission electron micrograph (TEM) using dark field mode of the collagen/HA composite scaffold mineralized for 24 hours via the static mineralization method.
FIG. 3D is a transmission electron micrograph (TEM) using dark field mode of the collagen/HA composite scaffold mineralized for 24 hours via the dynamic mineralization method.

To further confirm the intrafibrillar mineralization, Transmission Electronic Microscopy (TEM) analysis was employed to analyze the mineralized collagen/HA composite scaffolds 30. FIGS. 3A-3D show transmission electron micrographs of a mineralized collagen fiber using bright field (FIG. 3A), SAED (FIG. 3B), and dark field (FIG. 3C) modes in a composite mineralized for 24 hours via the static and dynamic (FIG. 3D) mineralization methods. FIGS. 3A-3D further confirm that the mineralization achieved by the PILP method is indeed intrafibrillar via both the static and dynamic mineralization methods. The selected area electron diffraction (SAED) pattern of FIG. 3B is very similar to that of bone, dominated by arcs of most of the crystal planes (i.e., 002, 004, etc. . . . ). Moreover, the longer axis of the HA crystals is parallel to the long axis of the collagen fiber, as illustrated by the bright crystal streaks seen throughout the dark field images of mineralized collagen via static (FIG. 3C) and dynamic (FIG. 3D) mineralization methods. The TEM dark field images and SAED pattern indicates the presence of intrafibrillar mineralization.

Figure 4A:
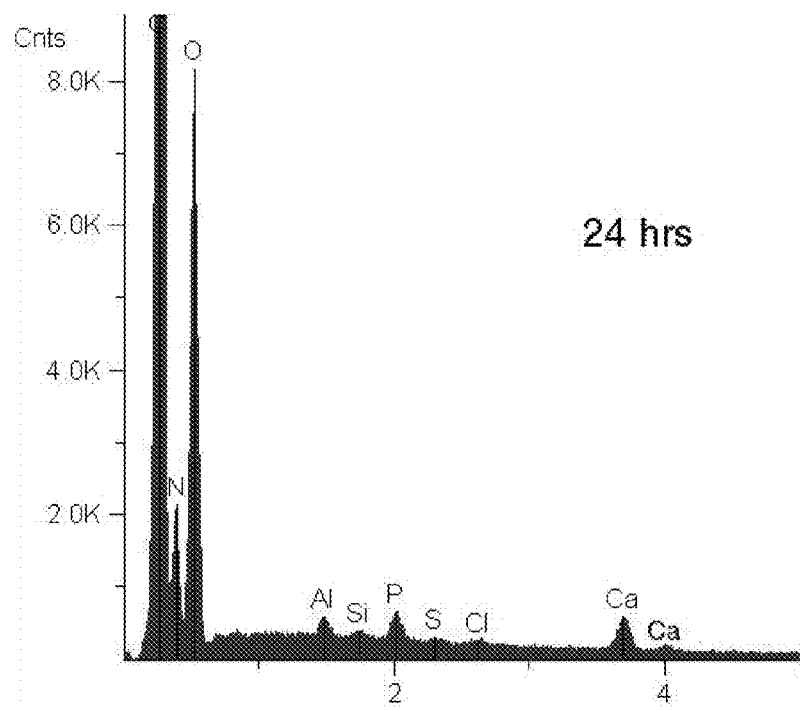
FIG. 4A is an energy dispersive spectra (EDS) graph of thin collagen/HA composite discs after static mineralization for 24 hours.
Figure 4B:
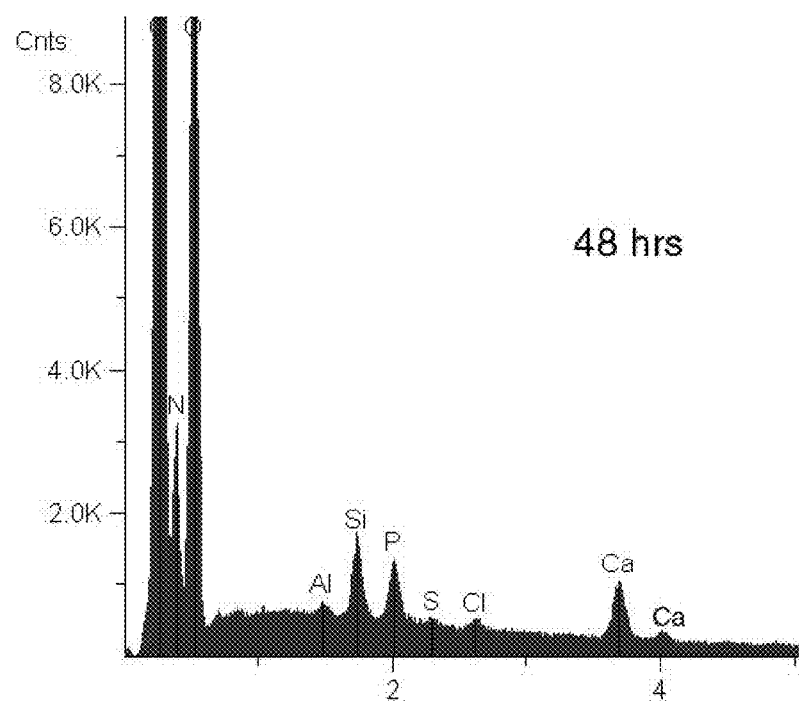
FIG. 4B is an energy dispersive spectra (EDS) graph of thin collagen/HA composite discs after static mineralization for 48 hours.
Figure 4C:
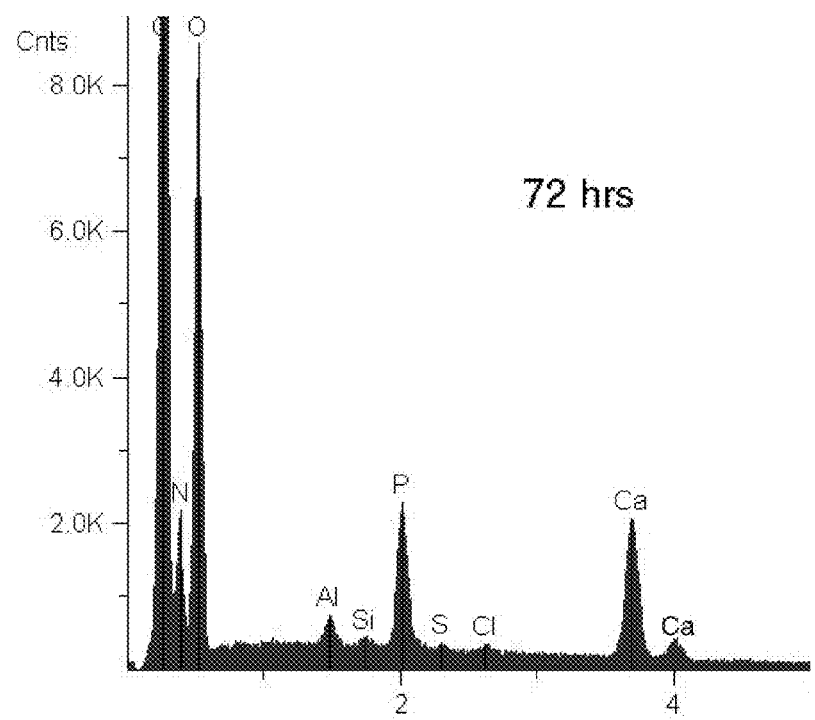
FIG. 4C is an energy dispersive spectra (EDS) graph of thin collagen/HA composite discs after static mineralization for 72 hours.

Moreover, the energy dispersive spectra (EDS) data shown in FIGS. 4A-4C demonstrate that, after mineralization, all the collagen/HA composite scaffolds 30 exhibited calcium and phosphorus elements. Furthermore, calcium-phosphorus peak amplitudes correspond to the mineralization time of the composites. More specifically, peak amplitude as illustrated increases with mineralization time.

Figure 5:
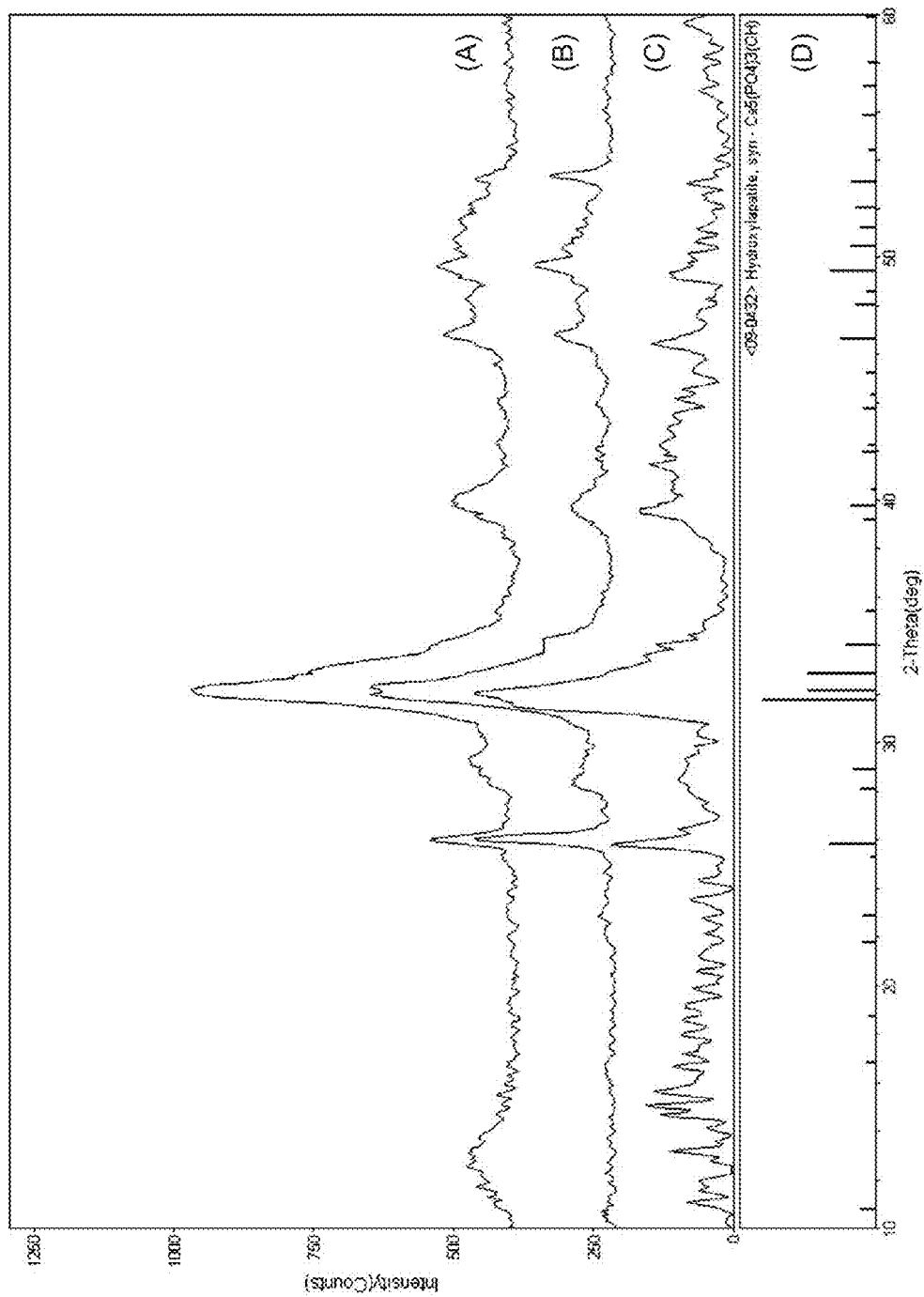
FIG. 5 is an X-ray diffraction spectra of (A) trabecular bone, (B) mineral solution precipitates, (C) 72 hour collagen/HA composite mineralized via a dynamic mineralization process/system, and (D) hydroxyapatite from The International Centre for Diffraction Data (ICDD) library.

Referring now to FIG. 5, the mineral phase analysis shown contains the X-ray diffraction (XRD) spectra obtained from (analysis A) samples of a trabecular bone, (analysis B) a precipitate from the mineral solution, and (analysis C) a collagen/HA composite mineralized for 72 hours via the dynamic process/system. The spectra were compared with the XRD spectrum of HA (analysis D) obtained from The International Centre for Diffraction Data (ICDD) library. The XRD spectra confirmed that the calcium-phosphate molecule is indeed hydroxyapatite. In addition, the similar XRD peak widths demonstrate that the collagen/HA composites possess small nanocrystals, similar to that of human trabecular bone.

The dynamic mineralization process also significantly increased the mechanical stiffness of the collagen scaffold as shown in the following Table of mechanical testing data. Furthermore, it is contemplated herein that the scaffold stiffness is controllable by the different mineralization rates and time as noted above, and as separately confirmed by FIG. 4.

| Sample | Stiffness (kPa) |
| --- | --- |
| Cross-linked Collagen | 6.7 ± 2.1 |
| 24-hr dynamic mineralization | 200.5 ± 129.4 |
| Trabecular bone | 10-2000 |

Figure 6:
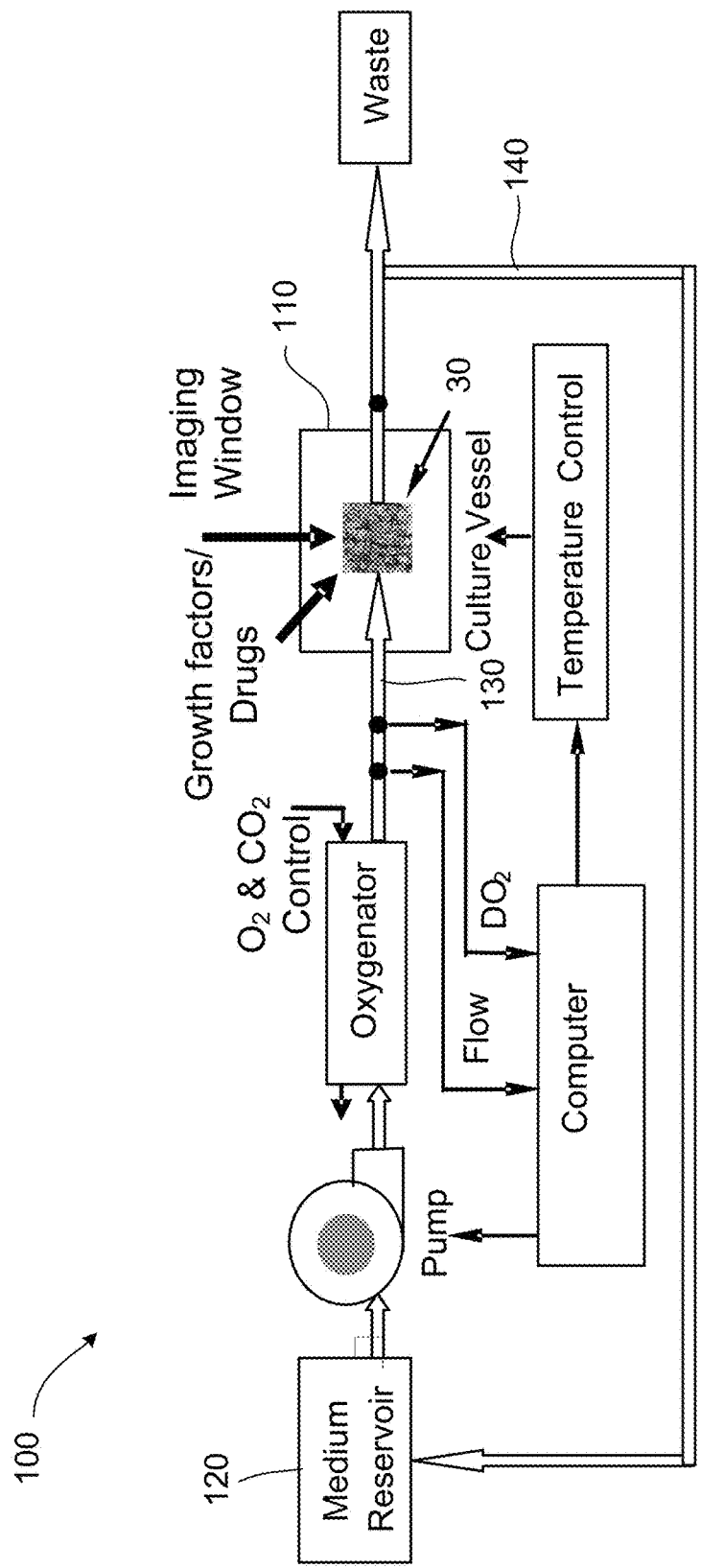
FIG. 6 is a schematic representation of a perfusion-flow/bioreactor (i.e., dynamic) system for cell culture on a 3D porous scaffold.
Figure 7A:
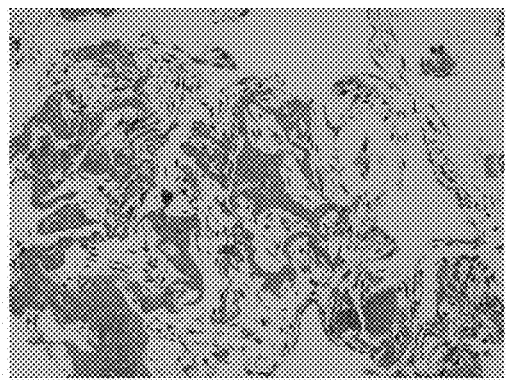
FIG. 7A is a hematoxylin and eosin (H&E) staining histology image illustrating remodeling of the collagen/HA composite scaffold and development of bone specific extracellular matrix by human mesenchymal stromal cells cultured on the scaffold at day 3.
Figure 7B:
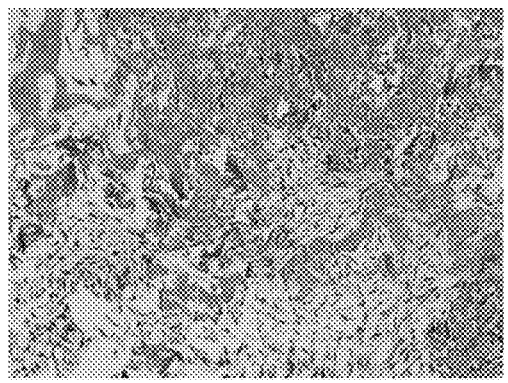
FIG. 7B is a hematoxylin and eosin (H&E) staining histology image illustrating remodeling of the collagen/HA composite scaffold and development of bone specific extracellular matrix by human mesenchymal stromal cells cultured on the scaffold at day 7.
Figure 7C:
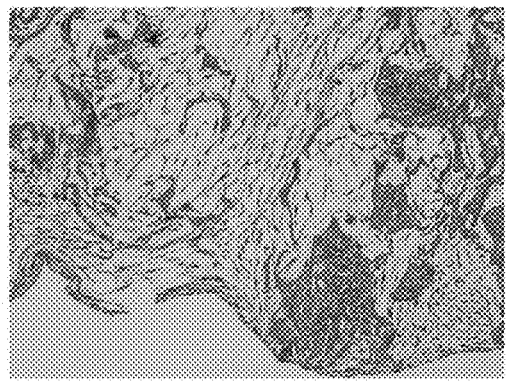
FIG. 7C is a hematoxylin and eosin (H&E) staining histology image illustrating remodeling of the collagen/HA composite scaffold and development of bone specific extracellular matrix by human mesenchymal stromal cells cultured on the scaffold at day 10.
Figure 7D:
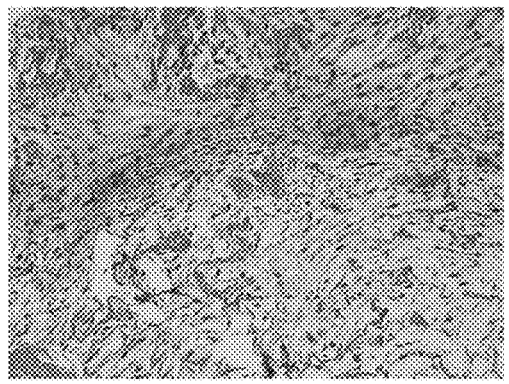
FIG. 7D is a hematoxylin and eosin (H&E) staining histology image illustrating remodeling of the collagen/HA composite scaffold and development of bone specific extracellular matrix by human mesenchymal stromal cells cultured on the scaffold at day 17.

Once the collagen/HA composite scaffold 30 is produced, living cells, such as bone tissue forming cells, may be provided thereon. Referring now to FIG. 6, there is shown a schematic of one preferable in vitro closed-loop perfusion-flow/bioreactor system 100 which may be used to continuously deliver oxygen and other nutrients to cells seeded/cultured on porous scaffolds, such as the collagen/HA composite scaffold 30. To further promote the remodeling of collagen/HA composite to bone extracellular matrix by the cells, such as human mesenchymal stromal cells, an osteogenic induction medium may be continuously circulated as the remodeling perfusate/perfusion fluid at a flow rate through the collagen/HA composite scaffold 30. An osteogenic induction medium may be understood as any medium provided that promotes the growth of bone tissue forming cells. For example, 0.01 µM of dexamethasone, 10 mM β-phosphoglycerol, and 50 µg/L of ascorbic acid will be supplemented into the medium. The flow rate may be on the order of 30-200 µm/s.

More particularly, after producing the collagen/HA composite scaffold 30, the composite scaffold 30 may be introduced to the in vitro closed-loop perfusion-flow/bioreactor system 100 by being placed in a perfusion chamber/culture vessel 110, and placed in fluid communication with a remodeling perfusion fluid 120, which may be circulated by the pump at a flow rate to deliver the remodeling perfusion fluid 120 to the composite scaffold 30.

Composite scaffold 30 may be in fluid communication with a fluid input passage 130 to provide the perfusion fluid 120 to the composite scaffold 30, cultured with, for example, human mesenchymal stromal cells. The perfusion fluid, after passing through the perfusion chamber/culture vessel 110 and collagen/HA composite scaffold 30, may be recirculated to a reservoir through passage 140. Other cells including osteoblast cells, osteoclast cells and/or osteoprogenitor cells, etc, may also be cultured on the collagen/HA composite scaffold.

As noted, perfusion fluid 120 may include one or more nutrients and oxygen to support the metabolism of cells and otherwise sustain the cells. The cells may proliferate within the collagen/HA composite scaffold 30 under continuous perfusion. The cells may specifically remodel the scaffold 30 and secrete bone extracellular matrix (ECM) within the scaffold 30, particularly by osteogenesis/ossification.

In various embodiments of the disclosure, the cells may be part of the remodeling perfusion fluid 120 and seeded on the scaffold 30 dynamically, or the cells may be first introduced and seeded/cultured on to the collagen/HA composite scaffold 30 statically before the scaffold 30 is placed in the perfusion chamber/culture vessel 110. More particularly, after producing the collagen/HA composite scaffold 30, cells may be introduced to and seeded/cultured on scaffold 30. Introduction and seeding of cells to scaffold 30 may be performed by applying a seeding suspension fluid to the scaffold 30 containing the cells.

Referring now to FIGS. 7A-7D, there are shown hematoxylin and eosin (H&E) staining histology images illustrating remodeling of the collagen/HA composite scaffold and development of bone specific extracellular matrix by human mesenchymal stromal cells cultured on the scaffold 30 with time. More particularly, FIGS. 7A-7D show H&E staining histology images at 3 days, 7 days, 10 days and 17 day, respectively.

Figure 8A:
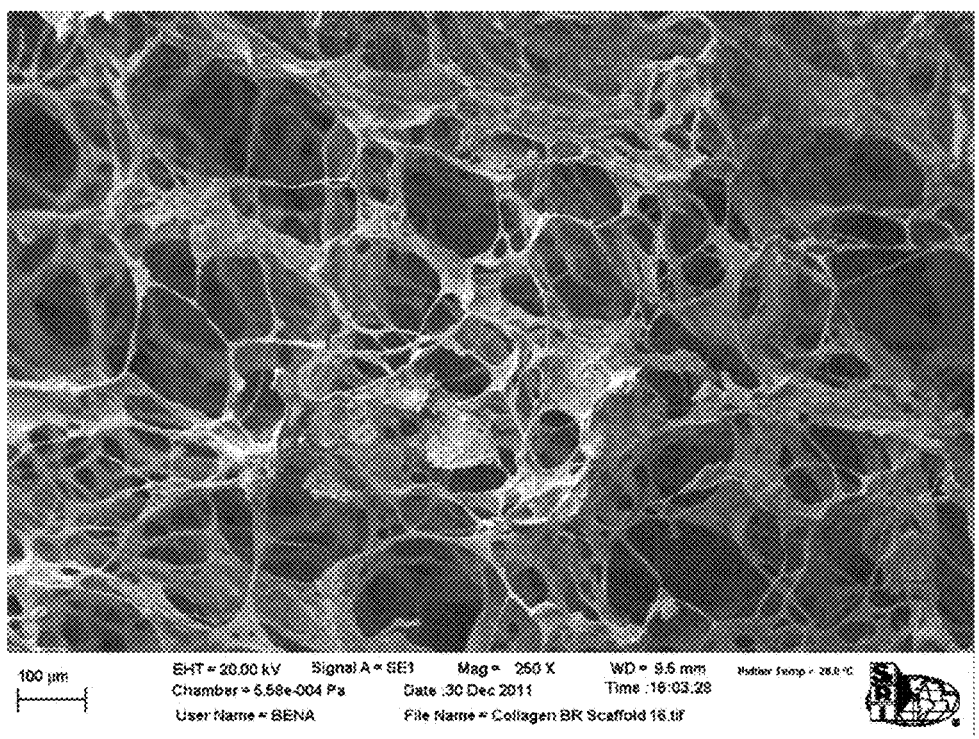
FIG. 8A is a scanning electron microscope (SEM) image of the collagen/HA composite scaffold before culture of human mesenchymal stromal cells on the collagen/HA composite scaffold.
Figure 8B:
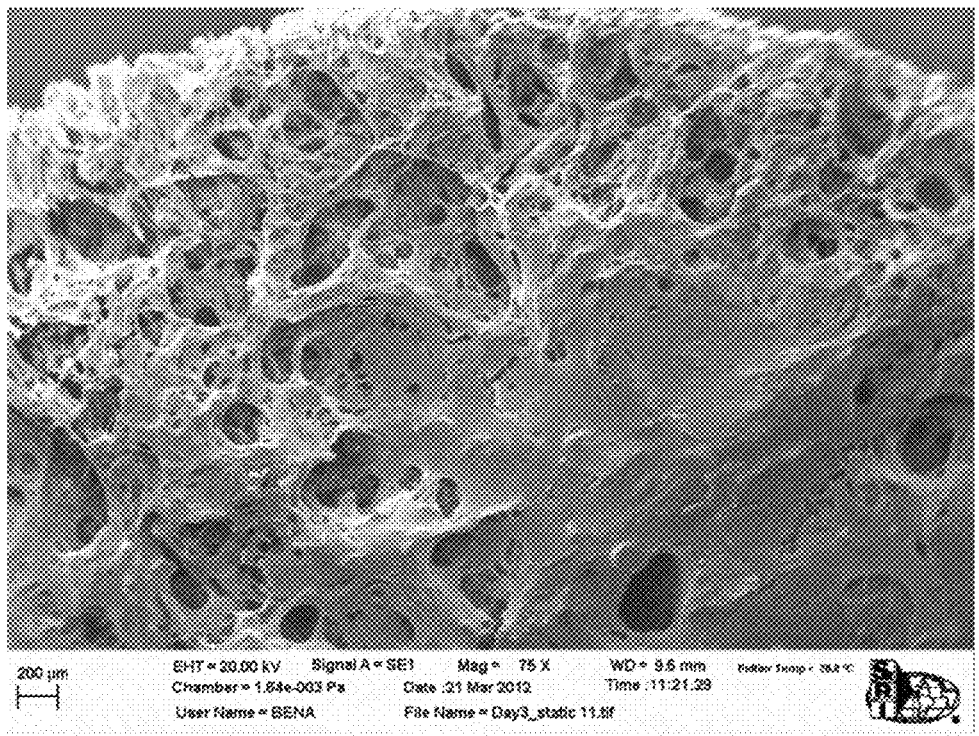
FIG. 8B is a scanning electron microscope (SEM) image of the collagen/HA composite scaffold 3 days after culture of human mesenchymal stromal cells on the collagen/HA composite scaffold.

Attention is now directed to FIGS. 8A and 8B, which illustrate the scanning electron microscope (SEM) images of development of extracellular matrix. FIG. 8A shows a scanning electron microscope (SEM) image of the collagen/HA composite scaffold before seeding/culture of human mesenchymal stromal cells on the collagen/HA composite scaffold. FIG. 8B shows a scanning electron microscope (SEM) image of the collagen/HA composite scaffold 3 days after seeding/culture of human mesenchymal stromal cells on the collagen/HA composite scaffold, and the development of bone specific extracellular matrix.

Figure 9A:
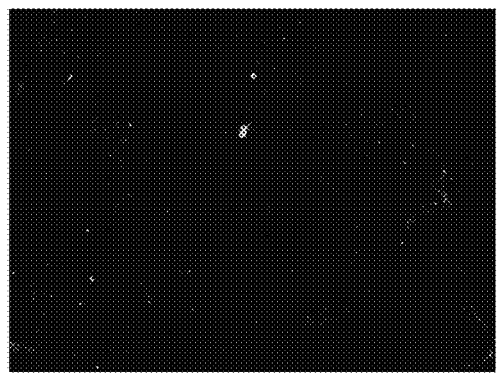
FIG. 9A is an immunofluorescence image of an isotype control.
Figure 9B:
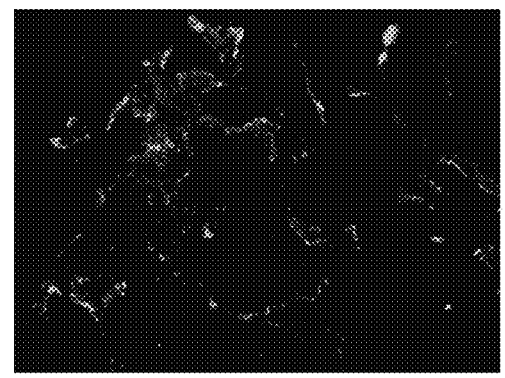
FIG. 9B is an immunofluorescence image of human collagen type I created by the human mesenchymal stromal cells cultured on the collagen/HA composite scaffold.
Figure 9C:
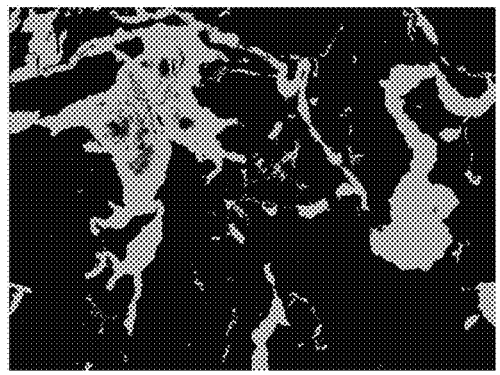
FIG. 9C is an immunofluorescence image of fibronectin created by the human mesenchymal stromal cells cultured on the collagen/HA composite scaffold.
Figure 9D:
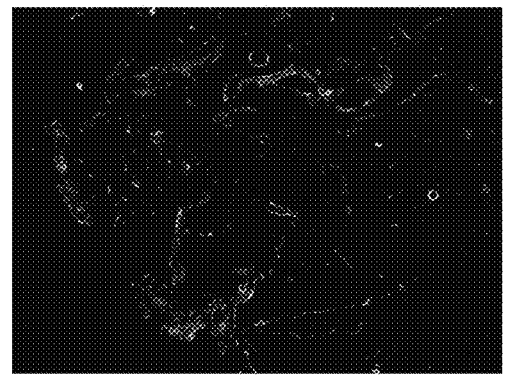
FIG. 9D is an immunofluorescence image of biglycan created by the human mesenchymal stromal cells cultured on the collagen/HA composite scaffold.

Referring to FIGS. 9A-9D, there are shown immunofluorescence images which illustrate the new extracellular matrix components created by the human mesenchymal stromal cells grown on the collage/HA composite scaffolds 30. FIG. 9A is an isotype control. FIG. 9B is an immunofluorescence image of human collagen type I created by the human mesenchymal stromal cells cultured on the collagen/HA composite scaffold. FIG. 9C is an immunofluorescence image of fibronectin created by the human mesenchymal stromal cells cultured on the collagen/HA composite scaffold. FIG. 9D is an immunofluorescence image of biglycan created by the human mesenchymal stromal cells cultured on the collagen/HA composite scaffold. These components are the major extracellular matrix components of bone.

Thereafter, delivery of the oxygen and one or more nutrients through the collagen/hydroxyapatite composite scaffold and the bone tissue forming cells may be terminated when the bone tissue forming cells have remodeled the collagen/hydroxyapatite composite scaffold with bone tissue extracellular matrix. It is contemplated herein that the remodeling of the composite scaffold can now be regulated to form a bone grafting material that has a stiffness, porosity level and/or pore size that is substantially similar in such characteristics (e.g. within 10% of average values) of a targeted bone material, such as trabecular bone from a selected anatomical location. Along such lines it is noted herein that via use of the dynamic perfusion method herein, a porosity level of 95% has been achieved with pore sizes of 250 μm. Accordingly, one may identify a targeted bone material and identify the stiffness (e.g. tensile strength or modulus values), porosity level and pore size characteristic of such targeted bone material and via the process of forming bone grafting material herein, select a flow rate and time for mineralization to achieve such goals.

As noted, to further develop an off-the-shelf bone grafting material, the remodeled collagen/HA scaffold 30 may be decellularized to create an acellular bone grafting material. In order to decellularize the remodeled collagen/HA scaffold 30, perfusion flow system 10 may be used again with a decellularization perfusion fluid (liquid solution) comprising at least one decellularization reagent which may be circulated by pump 16 to deliver the decellularization perfusion fluid to the remodeled collagen/HA scaffold 30, pass the fluid throughout the remodeled collagen/HA scaffold 30 and return the fluid to the source container 12 at a flow rate such that the cells are removed from the remodeled collagen/HA scaffold 30. The perfusion flow system is used again to deliver 2% SDS (sodium dodecyl sulfate) anionic surfactant, 1% triton X-100 ($C_{14}H_{22}O(C_2H_4O)n$) nonionic surfactant, 0.5 mg/mL DNase (deoxyribonuclease), 0.1 mg/mL RNase (ribonuclease), and rinse with fluid PBS (phosphate buffered saline) throughout the bone scaffold to eliminate cells and remnant DNAs.

Figure 10A:
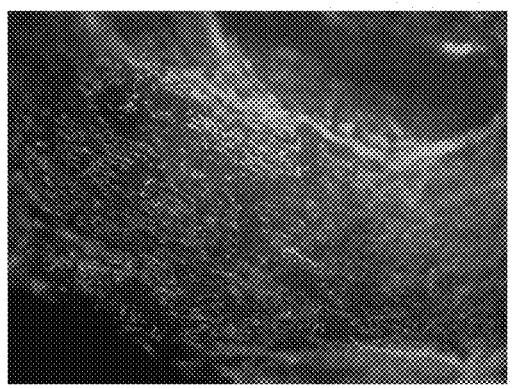
FIG. 10A is an immunofluorescence image of the collagen/HA composite scaffold before decellularization.
Figure 10B:
FIG. 10B is an immunofluorescence image of the collagen/HA composite scaffold after decellularization

Referring to FIGS. 10A-10B, there is shown immunofluorescence images of the remodeled collagen/HA scaffold before and after decellularization, respectively. The green fluorescence stains the cytoplasm of live cells. FIG. 10A is an immunofluorescence image of the collagen/HA composite scaffold after being cultured with cell for five weeks. After decellularization, all the cells and cell DNA are eliminated. The relatively bright spots in FIG. 10A indicate cells and the relatively dark image of FIG. 10B indicates that there are no cells.

Figure 11A:
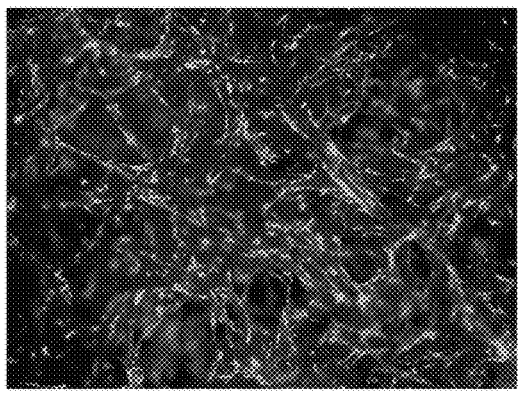
FIG. 11A is an immunofluorescence image of live cells (stained with green fluorescence) on the collagen/HA scaffold with no ECM (i.e. no remodeling)
Figure 11B:
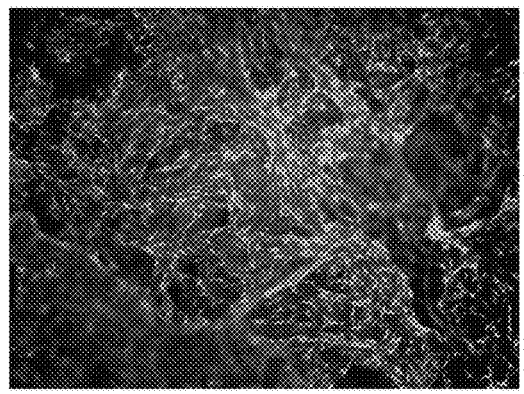
FIG. 11B is an immunofluorescence image of live cells (stained with green fluorescence) on the collagen/HA scaffold with decellularized ECM after 3 days.
Figure 11C:
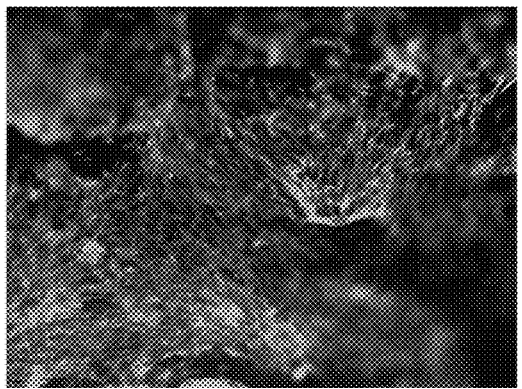
FIG. 11C is an immunofluorescence image of live cells (stained with green fluorescence) on the collagen/HA scaffold with decellularized ECM after 14 days.
Figure 11D:
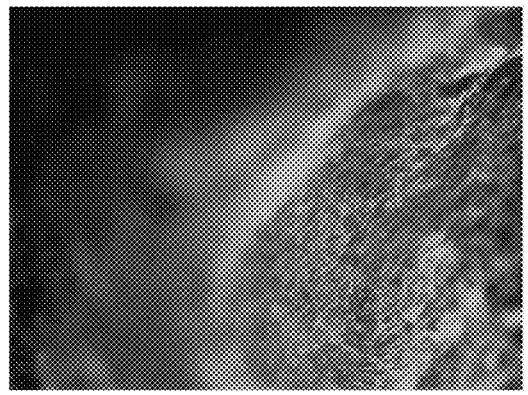
FIG. 11D is an immunofluorescence image of live cells (stained with green fluorescence) on the collagen/HA scaffold with decellularized ECM after 21 days.

The acellular collagen/HA scaffold 30, which may again be used as a bone grafting material with bone specific extracellular matrix, promotes cell re-organization and proliferation. Referring now to FIGS. 11A-11-D, FIG. 11A shows an immunofluorescence image of live cells (stained with green fluorescence) on the collagen/HA scaffold with no ECM (i.e. no remodeling). Conversely, FIGS. 11B-11D shows an immunofluorescence image of live cells (stained with green fluorescence) on the collagen/HA scaffold with decellularized ECM after 3 days, 14 days and 21 days, respectively. As shown, cells seeded on the decellularized ECM are better organized and have higher proliferation rate. Furthermore, the longer the formation of the ECM, or in other words, the more mature the ECM, the better the organization of the cells and the higher the density of the cells after a same period of culture.

The bone grafting material, whether the collagen/HA scaffolds containing bone cells derived ECM or not, may now be placed in a treatment site of a host to be treated. The cells seeded on the decellularized remodeled scaffold may be autologous cells of the host. The bone grafting material may be shaped to the tissue treatment site of the host, and the tissue treatment site may comprise a defect (e.g. void) in at least one bone of the host. The bone grafting material may provide at least one of osteoconduction, osteoinduction and osteogenesis.

As noted above, the bone grafting materials formed herein provide properties of stiffness as well as elasticity. Particularly, the stiffness of the grafting materials can be tuned with different length of mineralization. The stiffness may range from pure collagen scaffold of about 5 kP to around 2000 kP of trabecular bone. In addition, the elasticity of the composite scaffold allows it to be easily handled and shaped by the surgeons in the operating room to fit the tissue treatment site of a host.

While a preferred embodiment of the present invention(s) has been described, it should be understood that various changes, adaptations and modifications can be made therein without departing from the spirit of the invention(s) and the scope of the appended claims. The scope of the invention(s) should, therefore, be determined not with reference to the above description, but instead should be determined with reference to the appended claims along with their full scope of equivalents. Furthermore, it should be understood that the appended claims do not necessarily comprise the broadest scope of the invention(s) which the applicant is entitled to claim, or the only manner(s) in which the invention(s) may be claimed, or that all recited features are necessary.

What is claimed is:

1. A process to form a bone grafting material, comprising:
providing a porous collagen scaffold containing collagen fibers;
inserting the collagen scaffold into a perfusion chamber of a perfusion flow system;
continuously providing a mineralization perfusion fluid flow through the collagen scaffold at a flow rate through said collagen scaffold of 1 μm/s to 10 mm/s, said mineralization fluid containing an ion-containing extracellular fluid, which supplies mineral ions to said collagen scaffold such that hydroxyapatite (HA) crystals form on said collagen fibers and wherein said collagen scaffold has a geometry that inhibits said mineralization perfusion fluid from flowing around said scaffold rather than through said scaffold.

2. The process of claim 1 including:
providing the scaffold with bone tissue forming cells and delivering a perfusion fluid including oxygen and one or more nutrients through the collagen scaffold with said HA crystals and to the bone tissue forming cells at a flow rate such that the bone tissue forming cells remodel the collagen/hydroxyapatite composite scaffold and form a bone tissue extracellular matrix.

3. The process of claim 2 wherein said bone tissue extracellular matrix is decellularized and forming an acellular bone repair scaffold.

4. The process of claim 3 wherein the acellular bone repair scaffold is placed in a treatment site of a host to be treated.

5. The process of claim 2 wherein said perfusion fluid including oxygen and one or more nutrients comprises an osteogenic induction medium.

6. The process of claim 1 wherein said mineralization perfusion fluid is provided at a continuous flow rate of 20 µm/s to 500 µm/s.

7. The process of claim 1 wherein said mineralization perfusion fluid is provided at a continuous flow for a period of 12 hours to 7 days.

8. The process of claim 1 wherein said collagen scaffold has an outer portion and an inner portion and said hydroxyapatite crystals are deposited on said inner portion and outer portion, wherein said hydroxyapatite crystals are deposited substantially uniformly through the collagen scaffold.

9. The process of claim 1 wherein said perfusion flow system comprises a closed-loop perfusion flow system comprising a source container for said mineralization perfusion fluid, a pump to continuously provide said mineralization fluid to said collagen scaffold and a temperature controlled chamber to pass said mineralization fluid through said collagen scaffold and return said mineralization fluid to said source container.

10. The process of claim 9 wherein said temperature controlled chamber is maintained at body temperature.

11. A process to form a bone grafting material, comprising:
providing a porous collagen scaffold containing collagen fibers;
inserting the collagen scaffold into a perfusion chamber of a perfusion flow system;
continuously providing a mineralization perfusion fluid flow through the collagen scaffold at a flow rate through said collagen scaffold of 1 µm/s to 10 mm/s, said mineralization fluid containing an ion-containing extracellular fluid, which supplies mineral ions to said collagen scaffold such that hydroxyapatite crystals form on said collagen fibers and wherein said collagen scaffold has a geometry that inhibits said mineralization perfusion fluid from flowing around said scaffold rather than through said scaffold;
providing the collagen scaffold with said HA crystals with bone tissue forming cells and delivering a perfusion fluid including oxygen and one or more nutrients through the collagen scaffold with said HA crystals and to the bone tissue forming cells at a flow rate such that the bone tissue forming cells remodel the collagen scaffold with said HA crystals and form a bone tissue extracellular matrix; and
removing said bone tissue extracellular matrix and forming an acellular bone repair scaffold.

12. The process of claim 11 wherein said mineralization perfusion fluid is provided at a continuous flow rate of 20 µm/s to 500 µm/s.

13. The process of claim 11 wherein said mineralization perfusion fluid is provided at a continuous flow for a period of 12 hours to 7 days.

14. The process of claim 11 wherein said perfusion fluid including oxygen and one or more nutrients comprises an osteogenic induction medium.

15. The process of claim 11 wherein the acellular bone repair scaffold is placed in a treatment site of a host to be treated.

* * * * *